United States Patent
Spitzer et al.

(10) Patent No.: US 8,494,645 B2
(45) Date of Patent: Jul. 23, 2013

(54) COCHLEAR IMPLANT STIMULATION ARTIFACTS

(75) Inventors: Philipp Spitzer, Innsbruck (AT); Florian Feichtner, Igls-Vill (AT)

(73) Assignee: Med-El Elektromedizinische Geraete GmbH, Innsbruck (AT)

(*) Notice: Subject to any disclaimer, the term of this patent is extended or adjusted under 35 U.S.C. 154(b) by 868 days.

(21) Appl. No.: 12/270,428

(22) Filed: Nov. 13, 2008

(65) Prior Publication Data
US 2009/0125081 A1   May 14, 2009

Related U.S. Application Data

(60) Provisional application No. 60/987,936, filed on Nov. 14, 2007.

(51) Int. Cl.
*A61N 1/05* (2006.01)
(52) U.S. Cl.
USPC ............................................. 607/55; 607/137
(58) Field of Classification Search
USPC .............. 607/2, 27, 28, 55, 56, 115, 136, 137
See application file for complete search history.

(56) References Cited

U.S. PATENT DOCUMENTS

| | | | | |
|---|---|---|---|---|
| 4,527,567 A * | 7/1985 | Fischler et al. | ........... | 607/27 |
| 5,626,629 A | 5/1997 | Faltys et al. | ........... | 607/57 |
| 5,938,691 A | 8/1999 | Schulman et al. | ........... | 607/57 |
| 6,195,585 B1 | 2/2001 | Karunasiri et al. | ........... | 607/57 |
| 6,415,185 B1 * | 7/2002 | Maltan | ........... | 607/57 |
| 6,428,484 B1 * | 8/2002 | Battmer et al. | ........... | 600/554 |
| 6,600,955 B1 * | 7/2003 | Zierhofer | ........... | 607/57 |
| 7,016,731 B2 * | 3/2006 | Ryan et al. | ........... | 607/27 |
| 7,382,850 B2 * | 6/2008 | Zierhofer | ........... | 375/377 |
| 7,567,840 B2 * | 7/2009 | Armstrong | ........... | 607/27 |
| 7,787,952 B2 * | 8/2010 | Brodnick et al. | ........... | 607/28 |
| 2006/0025828 A1 * | 2/2006 | Armstrong et al. | ........... | 607/28 |
| 2006/0247735 A1 | 11/2006 | Honert | ........... | 607/57 |
| 2007/0244410 A1 * | 10/2007 | Fridman et al. | ........... | 600/554 |

OTHER PUBLICATIONS

Brown, Carolyn J., et al, "Electrically Evoked Whole Nerve Action Potential in Ineraid Cochlear Implant Users: Responses to Different Stimulating Electrode Configurations and Comparison to Psychophysical Responses", *Journal of Speech and Hearing Research*, vol. 39, Jun. 1996, pp. 453-467.

Gantz, Bruce J., et al, "Intraoperative Measures of Electrically Evoked Auditory Nerve Compound Action Potential", *The American Journal of Otology*, vol. 15, No. 2, Mar. 1994, pp. 137-144.

Guedes, Mariana C., et al, "Neural Response Telemetry Measures in Patients Implanted with Nucleus 24®", *Revista Brasileira de Otorrinolaringologia*, vol. 71, No. 5, Sep. 2005, pp. 660-667, XP002515865, ISSN: 0034-7299, sections "Material and method", "Results", "Discussion".

(Continued)

*Primary Examiner* — Brian T Gedeon
(74) *Attorney, Agent, or Firm* — Sunstein Kann Murphy & Timbers LLP

(57) ABSTRACT

An artifact monitoring stimulation system and corresponding method are described. An implantable electrode stimulator applies an electrical stimulation pulse to target tissue using implantable electrode contacts. An artifact monitor module monitors the electrode contacts during and after the stimulation pulse to observe an artifact signal resulting from the stimulation pulse to determine a operating characteristic associated with the stimulation system, the stimulated tissue and/or electrode-electrolyte interface properties.

22 Claims, 5 Drawing Sheets

OTHER PUBLICATIONS

Klop, W. Martin C., et al, "A New Method for Dealing with the Stimulus Artefact in Electrically Evoked Compount Action Potential Measurements", *Acta Oto-Laryngologica*, Scandinavian Univ. Press, Oslo, NO. vol. 124, No. 2, Mar. 1, 2004, pp. 137-143, XP009112350, ISSN: 0001-6489, abstract sections "Introduction", "Results—Artefact".

Ragheb, T., et al, "The Polarization Impedance of Common Electrode Metals Operated at Low Current Density", *Annals of Biomedical Engineering* Pergamon Press, Oxford, GB, vol, 19, No. 2, Jan. 1, 1991, pp. 151-163, XP009112328, ISSN: 0090-6964 cited in the application the whole document.

International Searching Authority, International Search Report and Written Opinion, PCT/US2008/083371, Mar. 4, 2009.

* cited by examiner

COCHLEAR IMPLANT STIMULATION ARTIFACTS

This application claims priority form U.S. Provisional Patent Application 60/987,936, filed Nov. 14, 2007, which is incorporated herein by reference.

FIELD OF THE INVENTION

The present invention relates to implantable medical devices, and more specifically, analysis of stimulation artifacts associated with such devices.

BACKGROUND ART

Electrode contacts of medical devices, such as cochlear implants have capacitive and resistive aspects of the interface between the electrode contact and the tissue, and these values are worth knowing for several reasons, e.g. detection of high impedance or short circuit electrodes, decision not to use electrodes, model calculations in research, etc. Electrode tissue interfaces commonly are based on purely resistive models. But it is known that there are also capacitive contributions to the impedance and that the interface behaves in a nonlinear way. See, for example, Ragheb, T. & Geddes, L. A., "The Polarization Impedance Of Common Electrode Metals Operated At Low Current Density," *Annals of Biomedical Engineering (ABME)*, 1991, 19, 151-163; Lai, W. & Choi, C. T. M. "Incorporating the Electrode-Tissue Interface to Cochlear Implant Models," *IEEE Transactions on Magnetics*, 2007, 43, 1721-1724; Fridman, G. Y. & Karunasiri, R. T., Removing Artifact in Evoked Compound Action Potential Recordings in Neural Stimulators," US Patent Application 20070244410; all of which are hereby incorporated by reference.

When a malfunction of an implantable medical device is suspected—for example, a stimulation malfunction in a cochlear implant—then information about the actual operation of the system is needed. There are various existing approaches to detecting malfunctions in implanted medical devices. For example, external amplifiers have been used to detect stimulation pulses by attaching external amplifier electrodes to the skin and synchronizing the signal recording with application of the suspicious stimulation signal. Some disadvantages of this method are that the equipment often is not locally available and has to be shipped, a specialist has to do the recordings, and the recording itself is not easy to do because of the skin electrodes and the necessary synchronization.

Another approach is based on the use of "telemetry" recordings where the implant itself records the voltage of the current source during a stimulation pulse. See, for example, U.S. Pat. No. 5,938,691, "Multichannel Implantable Cochlear Stimulator," which is hereby incorporated by reference. This can work well, but has some limitations (depending on the type of implant) such as only providing information about the resistive component of the current path over the electrodes.

Telemetry data has also been used U.S. Patent Publication 20060247735 by Honert described measuring stimulation currents for stimulating and non-stimulating electrodes to produce a matrix of impedance values. The impedance matrix is used to calculate electrode currents that are required to produce a desired pattern of stimulation voltage in the cochlea.

SUMMARY OF THE INVENTION

Embodiments of the present invention are directed to an artifact monitoring stimulation system and corresponding method. An implantable electrode stimulator applies an electrical stimulation pulse to target tissue. And an artifact monitor monitors the target tissue during and after the stimulation pulse to observe an artifact signal resulting from the stimulation pulse to determine characteristics of the electrode tissue interface and an operating characteristic of the artifact monitoring stimulation system.

In further specific embodiments, the operating characteristic may include a recording characteristic associated with a telemetry measurement channel of the system and/or an electrode characteristic associated with the interaction of the electrode stimulator with the target tissue. The electrode characteristic may include an interface capacitance associated with the interaction of the electrode stimulator with the target tissue and/or an RC time constant associated with the interaction of the electrode stimulator with the target tissue. Such recording of the characteristics of the electrode-tissue interface provides more information than in prior arrangements, which allows more realistic modeling of the system operation. In some embodiments, the operating characteristic may be used to determine customized stimulation parameters such as customized stimulation rates.

Embodiments may also identify an abnormal condition of the stimulation system based on the operating characteristic; for example, a high impedance or a short circuit condition. In specific embodiments, an existing evoked compound action potential (ECAP) measurement arrangement can be used to monitor the target tissue. The electrode stimulator may be a cochlear implant stimulator.

DETAILED DESCRIPTION OF SPECIFIC EMBODIMENTS

Figure 1:
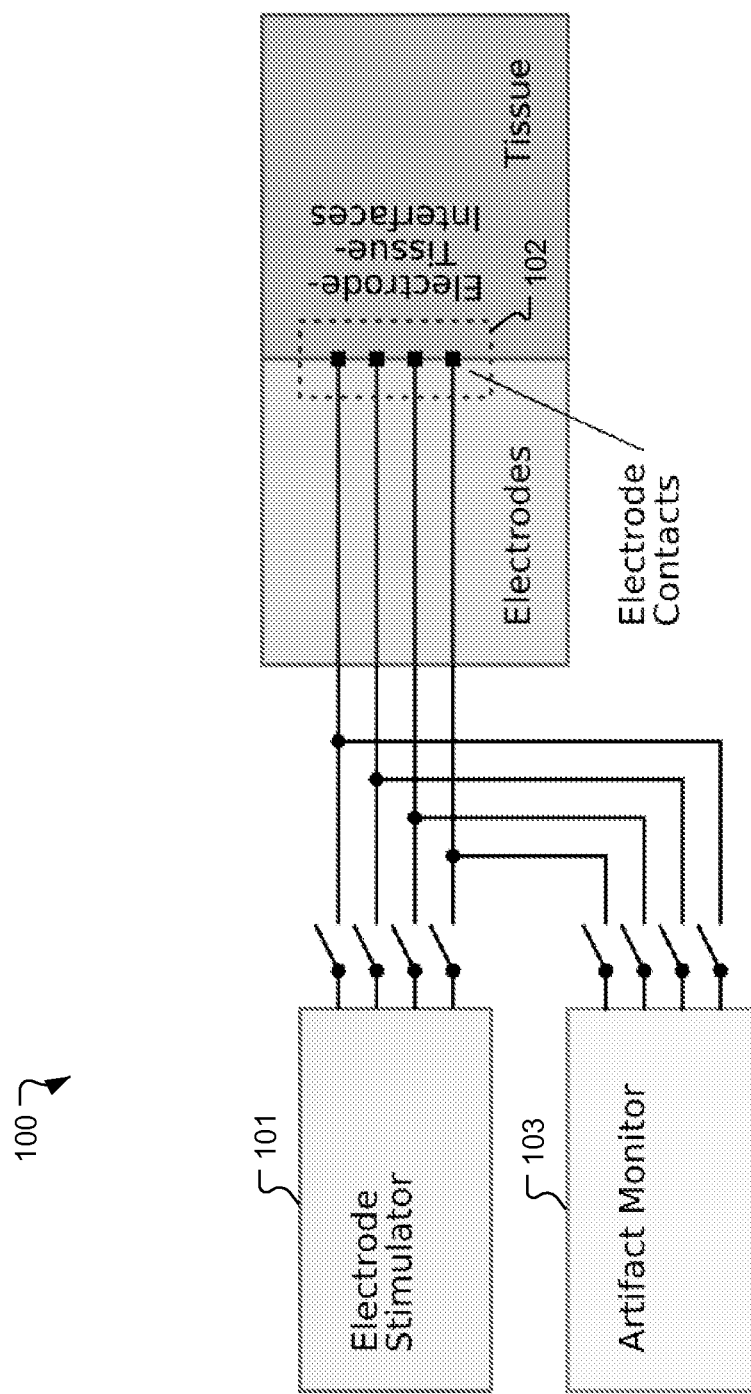
FIG. 1 shows an overview of one embodiment of an artifact monitor stimulation system.

Whereas prior implant telemetry systems could determine the resistive component of the electrode-tissue interface, embodiments of the present invention can further determine the capacitive component of the interface to discover characteristics such as the electrode charge decay time constant and/or the electrode-tissue capacity. The following discussion is presented in terms of the specific case of models based on a single resistance value and a single capacitive value. However, embodiments of the present invention in some specific applications may include models that use multiple resistance and/or capacitance values. Moreover, measurements of the capacitance and resistance components associated with the signal artifact may be very useful in other circumstances beyond the fit adjustment process. For example, during insertion of the stimulation electrode into the cochlea, continuous monitoring may be very useful to determine proper placement of orientation of the electrode in its intended position.

Modern cochlear implants are able to record evoked compound action potential (ECAP) signals of the auditory nerve. Usually this is used to record the neural response directly after a stimulation pulse. The ECAP signal is relatively small (typically only a few hundred μV) and recording the neural response is relatively difficult due to artifacts arising from the stimulation pulse, characteristics of the recording system, and external influences. But there are various methods to reduce or mathematically "subtract" these artifacts.

In a linear system, the normally unwanted artifact of a stimulation pulse is approximately an exponentially decaying voltage and various properties of the artifact can be used to gather information about the stimulation and/or the electrode-tissue interface. For example, the stimulation artifact may or may not increase with increasing stimulation pulse amplitude. And the direction of the stimulation artifact depends on the pulse phase sequence—for linear systems, cathodic-anodic biphasic pulses are opposite in voltage to anodic-cathodic biphasic pulses. Also, the decay time constant of the artifact contains information about the capacitive components in the circuit, including the electrode-tissue interface. Together with a traditional telemetry recording, analysis of the stimulation artifacts makes it possible to determine separate resistive and capacitive components of the electrode-tissue interface. Variation in the capacitances associated with the electrode-tissue interface may be due, for example, to variations associated with the various surrounding materials that contact with the implanted electrode: perilymphe, neural tissue, air, etc.

Where stimulation artifacts normally are undesirable, embodiments of the present invention make use of such artifacts and record them to determine operating characteristics and identify abnormal or malfunctioning elements of the implant system. In further specific embodiments, the operating characteristic may include a recording characteristic associated with a telemetry measurement channel of the system and/or an electrode characteristic associated with the interaction of the electrode stimulator with the target tissue.

FIG. 1 shows one embodiment of an artifact monitoring stimulation system 100, specifically, a cochlear implant. An electrode stimulator module 101 produces electrical stimulation pulses which are applied by electrode contacts 102 implanted in target neural tissue. An artifact monitor module 103 monitors the target tissue during and after the stimulation pulse to observe an artifact signal resulting from the stimulation pulse to determine a operating characteristic of the stimulation system 100. When the target tissue is stimulated by the electrode contacts 102, implant telemetry components within the electrode stimulator module 101 can record the stimulation voltage that is applied. The output capacitance of the electrode stimulation module 101 is a known value. Together with the known stimulation current, the total impedance of the electrode contacts 102 can be calculated.

Figure 2:
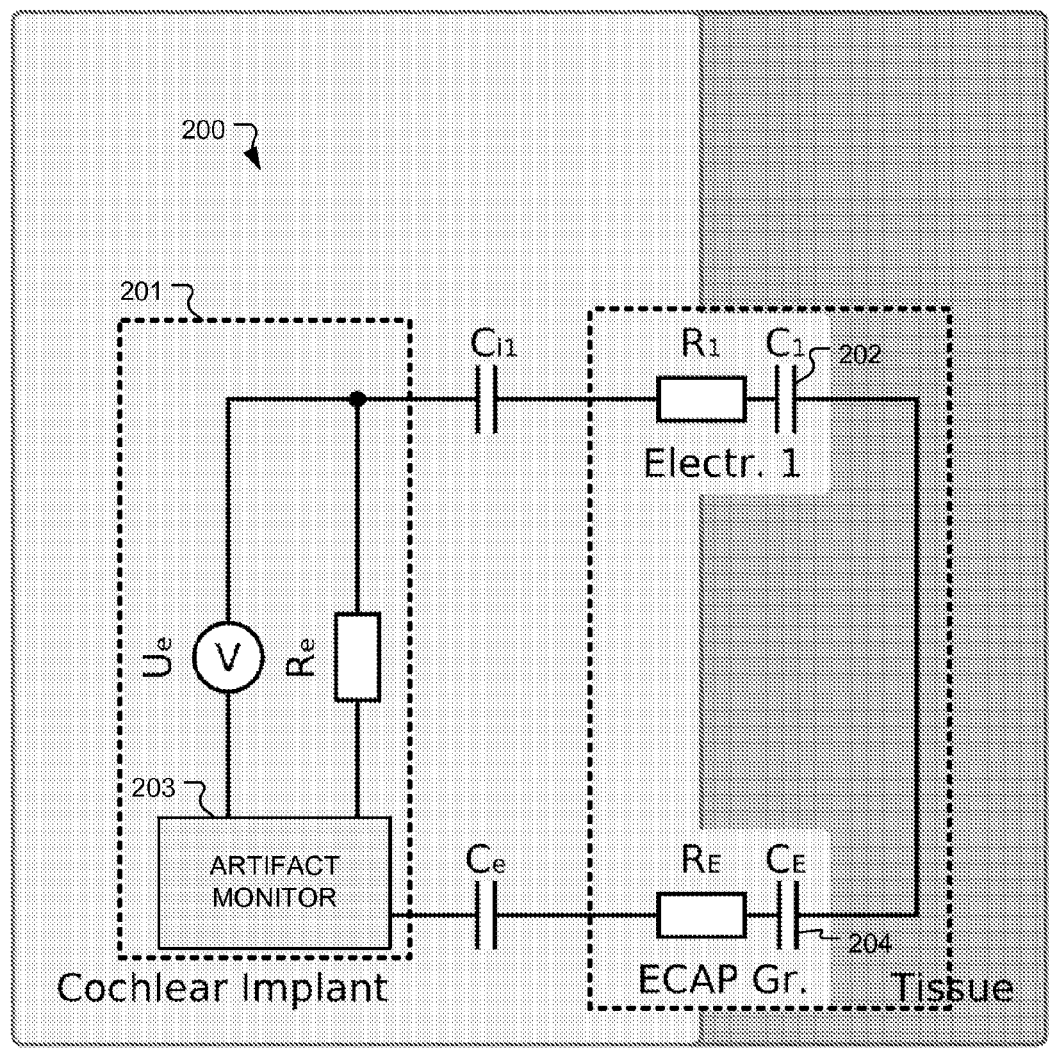
FIG. 2 shows an example based on an ECAP recording system where a different electrode is used as reference contact than the one used for stimulation.

FIG. 2 shows another specific embodiment of an artifact monitoring stimulation system 200 in which an artifact monitor module 203 based on an existing ECAP recording arrangement is used for monitoring the response associated with the stimulation system 200. Again an electrode stimulator module 201 produces electrical stimulation pulses that are applied to the target tissue by one or more implanted electrode contacts 202. One or more monitor electrodes 204 sense the resulting evoked compound action potentials (ECAPs) in the target tissue and provide a monitor signal back to the artifact monitor module 203. Also shown on FIG. 2 are simple equivalent circuit components associated with the various elements of the system. After the stimulation pulse is applied, the real and virtual capacitors stay charged and the discharge is observed with the existing ECAP recording arrangement. The time constant T of the exponential discharge can be determined and from that the product of the resistive and capacitive components of the circuit can be determined ($T=R*C$). The resistance R is known from the existing telemetry recording and therefore the total capacitance C can be determined. Using this method with other electrodes and parallel stimulation makes possible a determination of the individual electrode capacitances.

Figure 3:
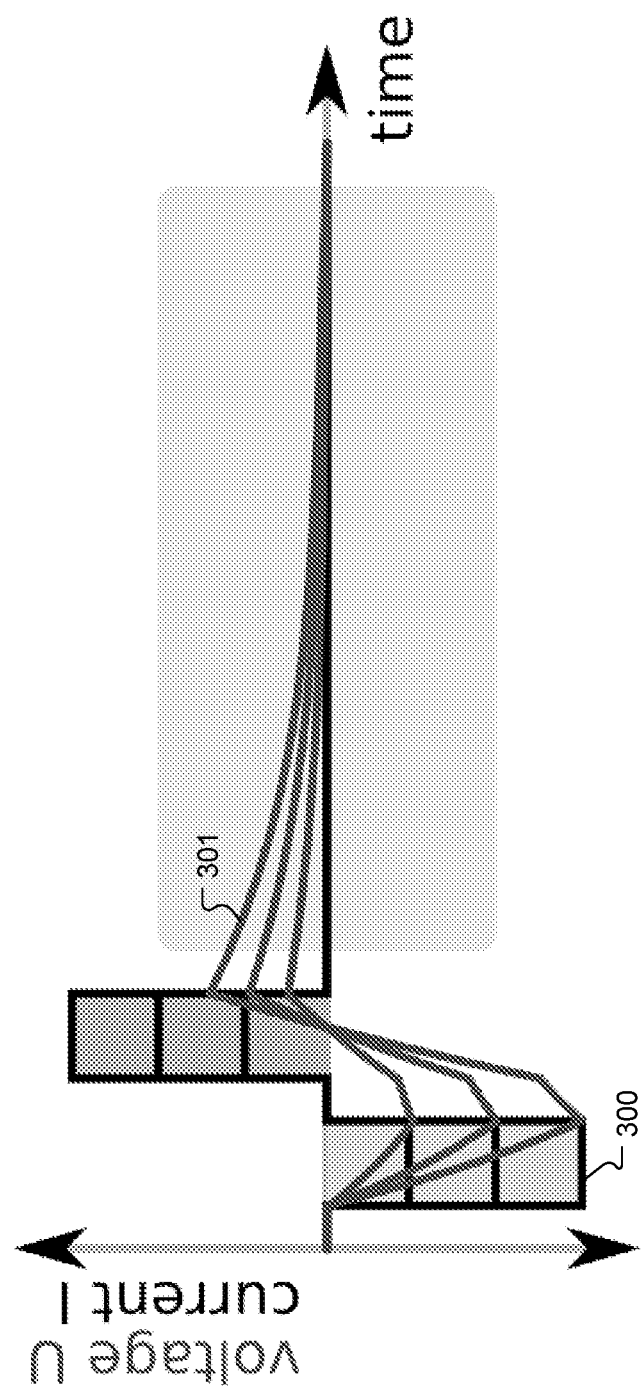
FIG. 3 shows a voltage waveform for a typical stimulation pulse sequence.
Figure 4:
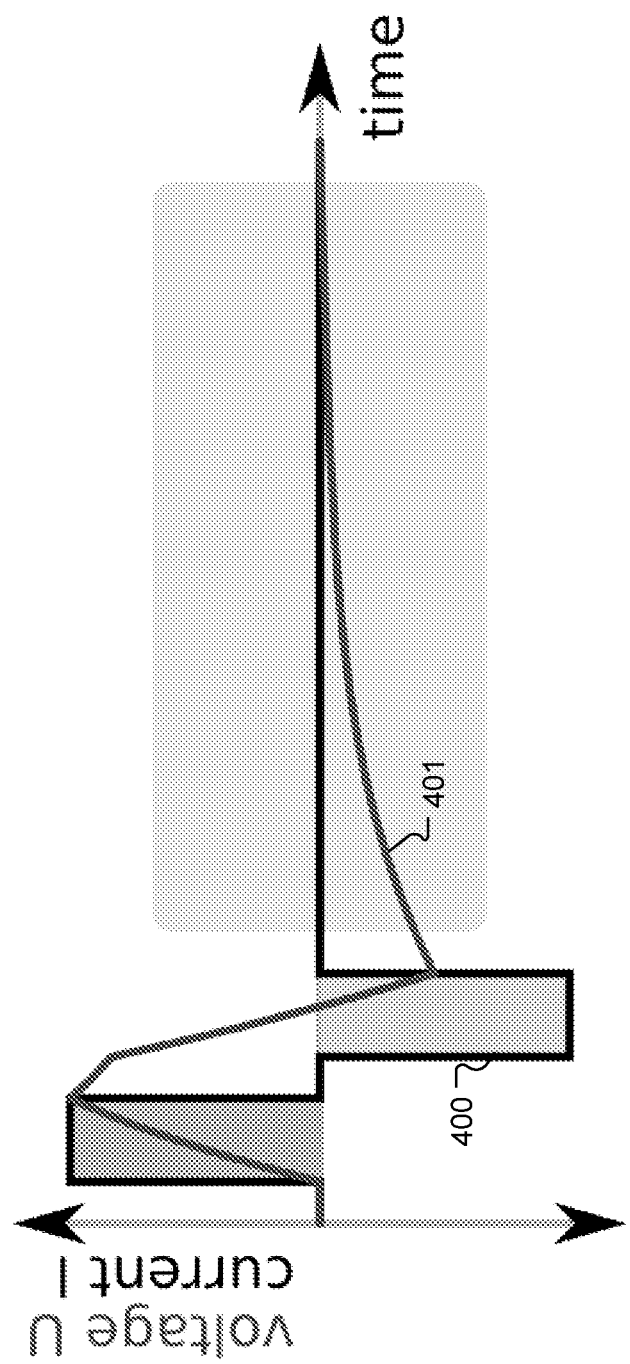
FIG. 4 shows that the specific direction of the artifact signal depends on the phase sequence.
Figure 5:
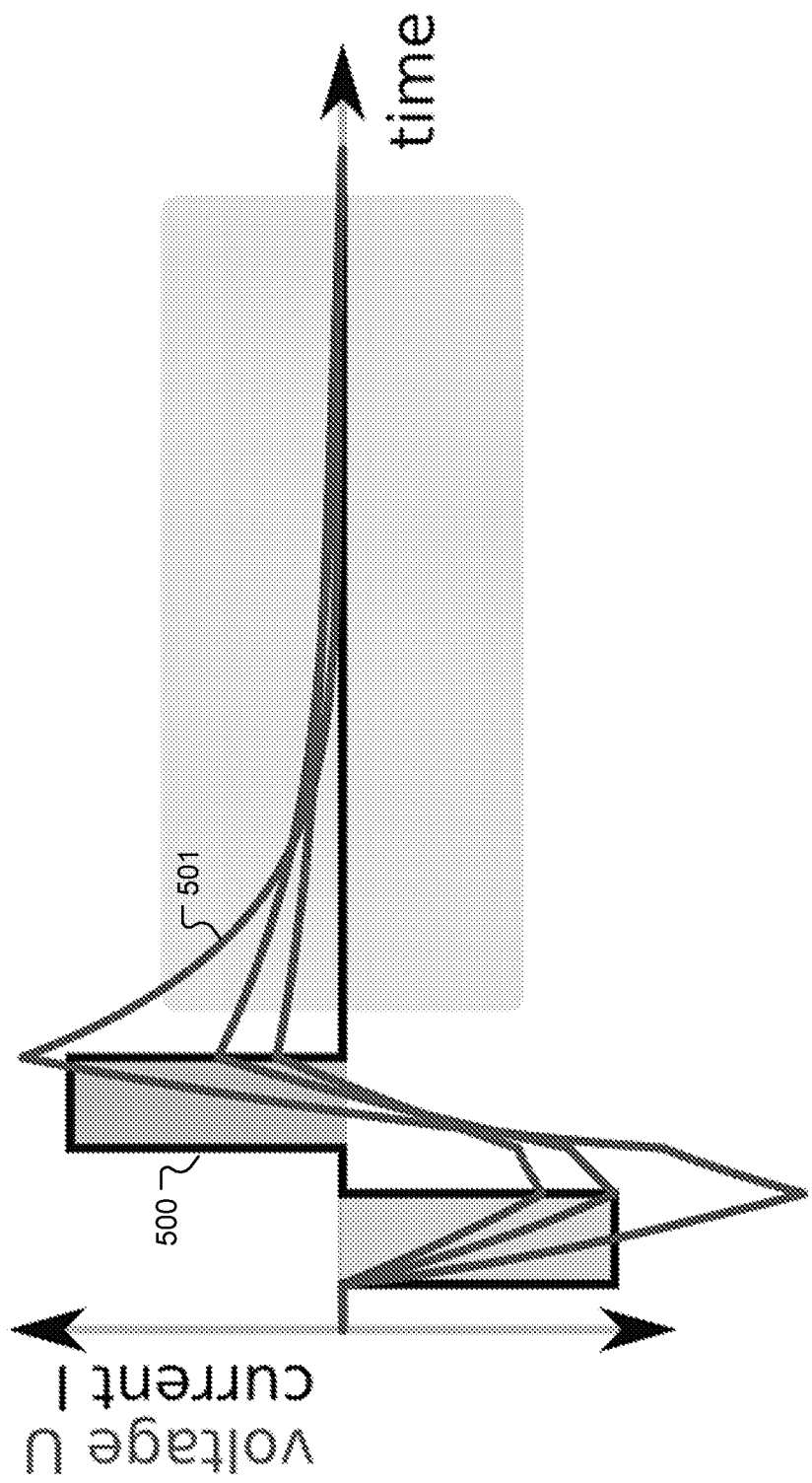
FIG. 5 shows how the time constant of the decaying residual charge depends on capacitance.

FIG. 3 shows an idealized voltage waveform for a typical stimulation pulse sequence for three different pulse amplitudes with the post-pulse voltage artifact exaggerated for emphasis. As shown in FIG. 3, when a bi-phase current pulse 300 is applied, a post-pulse voltage artifact signal 301 follows which is an exponentially decaying curve the amplitude of which is a function of the amount of current that is applied. FIG. 4 shows an opposite polarity pulse 400 demonstrating that the specific direction of the voltage artifact signal 401 depends on the phase sequence, cathodic-anodic or anodic-cathodic. As shown in FIG. 5, given a stimulation pulse 500 of a specified magnitude, the time constant of the decaying residual charge of the voltage artifact 501 depends on the capacity of the "circuit" (including the electrode/tissue interface).

Specific embodiments may also include a system function monitor, either within the electrode stimulation module or in a separate housing, for identifying an abnormal condition of the stimulation system based on the operating characteristic. For example, the system function monitor may detect a high impedance or a short circuit condition in various elements of the electrode stimulator and communicate the fault to an alarm register.

Embodiments allow for additional self-testing of implant system elements using ordinary implant software without extra hardware or specially trained persons. More detailed telemetry data is available and the additional capacitance information for the electrode-tissue interface could be useful to determine other operating characteristics of the electrode such as determination of rate or other subjective fitting properties. For example, the amount of sound detail that can be presented to the user may depend on the time constant, and a faster decay could offer more detail.

Moreover, measurements of the capacitance and resistance components associated with the signal artifact may be very useful in other circumstances beyond the fit adjustment process. For example, during insertion of the stimulation electrode into the cochlea, continuous monitoring may be very useful to determine proper placement of orientation of the electrode in its intended position.

Embodiments of the invention may be implemented in part using any conventional computer programming language. For example, preferred embodiments may be implemented in a procedural programming language (e.g., "C") or an object oriented programming language (e.g., "C++", Python). Alternative embodiments of the invention may be implemented as pre-programmed hardware elements, other related components, or as a combination of hardware and software components.

Embodiments can be implemented as a computer program product for use with a computer system. Such implementation may include a series of computer instructions fixed either on a tangible medium, such as a computer readable medium (e.g., a diskette, CD-ROM, ROM, or fixed disk) or transmittable to a computer system, via a modem or other interface device, such as a communications adapter connected to a network over a medium. The medium may be either a tangible medium (e.g., optical or analog communications lines) or a medium implemented with wireless techniques (e.g., microwave, infrared or other transmission techniques). The series of computer instructions embodies all or part of the functionality previously described herein with respect to the system. Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). Of course, some embodiments of the invention may be implemented as a combination of both software (e.g., a computer program product) and hardware. Still other embodiments of the invention are implemented as entirely hardware, or entirely software (e.g., a computer program product).

Although various exemplary embodiments of the invention have been disclosed, it should be apparent to those skilled in the art that various changes and modifications can be made which will achieve some of the advantages of the invention without departing from the true scope of the invention.

What is claimed is:

1. A method of measuring an operating characteristic of an implanted stimulation system, the method comprising:
    applying an electrical stimulation pulse to target tissue with a cochlear implant electrode contact;
    monitoring the electrode contact via a telemetry measurement channel of the system during and after the stimulation pulse to observe a time dependent artifact signal resulting from and immediately following the stimulation pulse; and
    using the time dependent characteristic of the observed artifact signal to determine a capacitance associated with the electrical interaction of the electrode contact with the target tissue.

2. A method according to claim 1, wherein determining the interface capacitance includes determining an RC time constant associated with the interaction of the electrode contact with the target tissue.

3. A method according to claim 1, further comprising:
    identifying an abnormal condition of the stimulation system based on the interface capacitance.

4. A method according to claim 3, wherein the abnormal condition includes one of a high impedance and a short circuit.

5. A method according to claim 1, wherein monitoring the target tissue is based on an evoked compound action potential (ECAP) measurement arrangement.

6. A method according to claim 1, further comprising:
    using the interface capacitance to fit the cochlear implant to a user.

7. A method according to claim 6, wherein the interface capacitance includes a recorded RC time constant of the electrode contact.

8. A method according to claim 6, wherein the interface capacitance is used to determine customized stimulation parameters.

9. A method according to claim 8, wherein the customized stimulation parameters include customized stimulation rates.

10. A method according to claim 1, further comprising:
    using the monitoring during insertion of the electrode stimulator for evaluating the placement and positioning of an electrode containing the electrode contact.

11. An artifact monitoring stimulation system, the system comprising:
    an implantable electrode stimulator for applying an electrical stimulation pulse to target tissue using a cochlear implant electrode contact; and
    an artifact monitor module for monitoring the electrode stimulator via a telemetry measurement channel of the system during and after the stimulation pulse to observe a time dependent artifact signal resulting from and immediately following the stimulation pulse to determine from the time dependent characteristic of the artifact signal an interface capacitance associated with the electrical interaction of the electrode contact with the target tissue.

12. A system according to claim 11, wherein determining the interface capacitance includes determining an RC time constant associated with the interaction of the electrode contact with the target tissue.

13. A system according to claim 11, further comprising:
    a system function monitor for identifying an abnormal condition of the stimulation system based on the interface capacitance.

14. A system according to claim 13, wherein the abnormal condition includes one of a high impedance and a short circuit.

15. A system according to claim 11, wherein the artifact monitor uses an evoked compound action potential (ECAP) measurement arrangement to monitor the target tissue.

16. A system according to claim 11, wherein the interface capacitance is adapted for fitting the cochlear implant to a user.

17. A system according to claim 16, wherein the interface capacitance includes a recorded RC time constant of the electrode contact.

18. A system according to claim 16, wherein the interface capacitance is adapted for determining customized stimulation parameters.

19. A system according to claim 18, wherein the customized stimulation parameters include customized stimulation rates.

20. A system according to claim 11, wherein the using the system function monitor is adapted for evaluating the placement and positioning of an electrode containing the electrode contact during insertion.

21. A method of measuring an operating characteristic of an implanted stimulation system, the method comprising:
    applying an electrical stimulation pulse to target tissue with a cochlear implant electrode contact;
    monitoring the electrode contact via a telemetry measurement channel of the system during and after the stimulation pulse to observe a time dependent artifact signal resulting from and immediately following the stimulation pulse; and
    using the time dependent characteristic of the observed artifact signal to determine a recording characteristic of the telemetry measurement channel.

22. An artifact monitoring stimulation system, the system comprising:
    an implantable electrode stimulator for applying an electrical stimulation pulse to target tissue using a cochlear implant electrode contact; and
    an artifact monitor module for monitoring the electrode stimulator via a telemetry measurement channel of the system during and after the stimulation pulse to observe a time dependent artifact signal resulting from and immediately following the stimulation pulse to determine from the time dependent characteristic of the artifact signal a recording characteristic of the telemetry measurement channel.

* * * * *